United States Patent
Chen

(10) Patent No.: US 10,117,910 B2
(45) Date of Patent: Nov. 6, 2018

(54) COMPOSITION OF NATURAL VITAMIN C AND FISH SCALE COLLAGEN PEPTIDE AND PREPARATION METHOD THEREOF

(71) Applicant: Hainan Meihetai Biotechnology Co., Ltd., Haikou (CN)

(72) Inventor: Gonghui Chen, Haikou (CN)

(73) Assignee: HAINAN MEIHETAI BIOTECHNOLOGY CO., LTD., Haikou (CN)

( * ) Notice: Subject to any disclaimer, the term of this patent is extended or adjusted under 35 U.S.C. 154(b) by 0 days.

(21) Appl. No.: 15/312,616

(22) PCT Filed: Feb. 4, 2015

(86) PCT No.: PCT/CN2015/072250
§ 371 (c)(1),
(2) Date: Nov. 18, 2016

(87) PCT Pub. No.: WO2015/176558
PCT Pub. Date: Nov. 26, 2015

(65) Prior Publication Data
US 2017/0087220 A1    Mar. 30, 2017

(30) Foreign Application Priority Data

May 20, 2014 (CN) .......................... 2014 1 0219053

(51) Int. Cl.
| | |
|---|---|
| C12P 21/06 | (2006.01) |
| A61K 38/39 | (2006.01) |
| A61K 31/375 | (2006.01) |
| A61K 35/60 | (2006.01) |
| A61K 36/185 | (2006.01) |
| C12P 17/04 | (2006.01) |
| C12P 21/00 | (2006.01) |
| A61K 36/736 | (2006.01) |

(52) U.S. Cl.
CPC ............ *A61K 38/39* (2013.01); *A61K 31/375* (2013.01); *A61K 35/60* (2013.01); *A61K 36/185* (2013.01); *A61K 36/736* (2013.01); *C12P 17/04* (2013.01); *C12P 21/005* (2013.01); *C12P 21/06* (2013.01); *C12Y 304/00* (2013.01); *A61K 2236/00* (2013.01)

(58) Field of Classification Search
None
See application file for complete search history.

(56) References Cited

FOREIGN PATENT DOCUMENTS

| | | | |
|---|---|---|---|
| CN | 200810197725.9 | | 4/2009 |
| CN | 101693108 | | 4/2010 |
| CN | 102429235 A | * | 5/2012 |
| CN | 102511669 A | * | 6/2012 |
| CN | 201110435489.1 | | 7/2012 |
| CN | 103993061 | | 8/2014 |
| JP | 2004238365 A | * | 8/2004 |
| WO | WO-2011145737 A1 | * | 11/2011 ............. A61K 31/05 |

OTHER PUBLICATIONS

Chinese First Office Action, dated Nov. 4, 2015, in Chinese Patent Application No. 201410219053.2, a related application, 11 pp. (with English translation).
Chinese Second Office Action, dated Jan. 8, 2016, in Chinese Patent Application No. 201410219053.2, a related application, 12 pp. (with English translation).
Chinese Third Office Action, dated Jun. 23, 2016, in Chinese Patent Application No. 201410219053.2, a related application, 13 pp. (with English translation).

\* cited by examiner

*Primary Examiner* — Lianko G Garyu
(74) *Attorney, Agent, or Firm* — Lathrop Gage LLP

(57) ABSTRACT

Disclosed is a composition of natural vitamin C and a fish scale collagen peptide, comprising the following components: natural vitamin C and a fish scale collagen peptide. Also disclosed is a method for preparing the above-mentioned composition.

16 Claims, No Drawings

COMPOSITION OF NATURAL VITAMIN C AND FISH SCALE COLLAGEN PEPTIDE AND PREPARATION METHOD THEREOF

CROSS-REFERENCE TO RELATED APPLICATIONS

This application is a U.S. National Stage Application filed under 35 U.S.C. § 371 of International Application No. PCT/CN2015/072250, filed Feb. 4, 2015, which claims the benefit of Chinese Application No. 201410219053.2, filed May 20, 2014. Both of these applications are hereby incorporated by reference in their entireties.

TECHNICAL FIELD

The present invention relates to the field of health care products, and particularly to a composition of natural vitamin C and a fish scale collagen peptide and to a preparation method thereof.

BACKGROUND ART

Vitamin C (VC) is also called as ascorbic acid. Some fruits and vegetables contain a great amount of natural vitamin C, such as cherries, kiwi fruits, tomatoes etc. With the expansion of the application range of vitamin C, synthetic vitamin C formulations are accepted by more and more people. However, vitamin C contained in natural food is totally different from synthetic vitamin C actually. In fruits and vegetables, natural vitamin C functions more efficiently as ascorbic acid with the assistance of rutin. Nevertheless, synthetic vitamin C is a pure chemical pharmaceutical formulation, the effect of which is far less than that of vitamin C. Moreover, the administration of a synthetic formulation often requires a great dosage, and in the case of long-term administration, oxalic acid would be formed in the body, while oxalic acid would bring about the potential threat of forming renal oxalate calculus. Nevertheless, natural vitamin C is exceedingly unstable, and would be easily oxidized and decomposed during processing and cooking, which results in a great loss during the preparation thereof into a formulation and greatly limits the industrial processing and wide application of natural vitamin C.

Collagen mainly exists in human body parts, such as skins, skeleton, eyes, teeth, tendons, viscera (including heart, stomach, intestines and blood vessels), and the function thereof lies in maintaining the morphology and structure of the skins and tissues and organs, and it is also an important raw material for the repair of a variety of tissue injuries. Collagen accounts for 70% of the components of human skin. Collagen is an important component necessary for maintaining normal activities of human body, and also a substance for keeping young and preventing aging in the meanwhile. Moreover, collagen also has the effects of preventing diseases, improving physical condition and so on, and has good cosmetological and health-caring functions. Collagen peptide is an extracellular protein, which is composed of more than three amino acids and prepared by the degradation processing of natural proteins. The absorption of protein by human body is realized in the form of a peptide, and due to the characteristics of its molecular structure and its relatively small molecular weight, the collagen peptide has good permeability and compatibility, and can be directly absorbed by human body without metabolism, which leads to an exceedingly high utilization efficiency in human body. Collagen peptide has significant effects in the aspects of improving skin conditions, delaying aging, and preventing and treating diseases such as osteoporosis.

DISCLOSURE OF THE INVENTION

The present invention provides a composition of natural vitamin C and a fish scale collagen peptide and a method of preparing the same, wherein the loss of the natural vitamin C during the preparation process can be reduced, the activity of the fish scale collagen peptide can be maintained, and end products have a homogeneous and stable quality.

The technical solution of the present invention is realized as follows:

A composition of natural vitamin C and a fish scale collagen peptide comprises the following components: natural vitamin C and a fish scale collagen peptide.

Further, the composition of natural vitamin C and a fish scale collagen peptide comprises the respective components by mass parts: 0.1-5 parts of the natural vitamin C and 98-99.9 parts of the fish scale collagen peptide.

Further, the molecular weight of the fish scale collagen peptide is 500-3,000 Dalton.

A method of preparing a composition of natural vitamin C and a fish scale collagen peptide comprises the following steps of:

(1) adding ultrapure water into a formula amount of the fish scale collagen peptide to prepare an aqueous solution;

(2) adding a pH regulator into the aqueous solution of the fish scale collagen peptide to adjust pH value to 5-7; and adding, under a negative pressure condition, a formula amount of the natural vitamin C to prepare a mixed solution of the natural vitamin C and the fish scale collagen peptide;

(3) concentrating the composition obtained in step (2) under a negative pressure to a concentrate of ¼-½ of the original volume; and (4) cold drying, freeze drying or spray drying the concentrate under a negative pressure condition, to give the composition of natural vitamin C and a fish scale collagen peptide.

Further, in said step (1), based on the total mass of the natural vitamin C and the fish scale collagen peptide, the mass of the ultrapure water is 5-7 times the total mass.

Further, the pH regulator used for adjusting pH value in said step (2) is citric acid or malic acid.

Further, in said step (1), step (2) and step (3), a temperature is controlled at 30-55° C. during the mixing and concentration processes.

Further, in said step (4), a temperature for spray drying is between 100 and 140° C.; a temperature is controlled at 40-52° C. during the process of cold drying; and a temperature is controlled at −20 to −10° C. during the process of freeze drying.

Further, the ranges of the negative pressures (P) in said steps (2), (3) and (4) are: $0.01\ \text{MPa} \leq P < 0.1\ \text{MPa}$.

Further, the natural vitamin C is extracted from Acerola cherry.

Further, a method of preparing the fish scale collagen peptide comprises the following steps of:

a. selecting fish scales as a raw material, and immersing the same in edible vinegar for softening under a negative pressure;

b. cleaning, drying and sterilizing the softened fish scales, and then adding water and an enzyme successively for enzymatic hydrolysis, wherein pressure is controlled as being negative during the enzymatic hydrolysis process;

c. adding activated carbon for decoloration and deodorization under a negative pressure, and filtering out insoluble substances, to give an enzymatic-hydrolyzed fish scale collagen peptide solution; and d. concentrating, under a negative pressure, said fish scale collagen peptide solution to 30-50% of the volume thereof, and obtaining the fish scale collagen peptide by falling film evaporation and drying.

Further, the ranges of the negative pressures (P) in said steps a, b, c and d are: $0.01 \text{ MPa} \leq P < 0.1 \text{ MPa}$.

Further, in said step a, temperature of softening is 70-90° C., and duration of softening is 30-50 min.

Further, in said step b, the weight of water added is 5-20 times that of the fish scales, and the weight of the enzyme added is 1%-4% of that of the fish scales, and the enzymatic hydrolysis is performed at a temperature controlled at 30-50° C., for 2-6 h.

Further, the enzyme is selected from the group consisting of neutral proteases and alkali proteases.

Further, in said step c, a proportion of the added activated carbon to the weight of the fish scales is 1%-4%, and the decoloration and deodorization are performed at a temperature controlled at 20-30° C., for 30-40 min.

Further, in said step d, a temperature is controlled at 60-70° C. during the concentration process, and a temperature is controlled at 100-140° C. during the drying process.

The beneficial effects of the present invention are as follows:

As the natural vitamin C is exceedingly unstable in nature, it would be easily oxidized and decomposed during the preparation process and thus lose its activity. As to the production method of the composition of natural vitamin C and a fish scale collagen peptide provided in the present invention, the whole production process is performed under a negative pressure and at a low temperature, and no addition of further additives is required, thus, the natural vitamin C can be preserved to the greatest degree. The resulting end product has the health caring functions of both fish scale collagen peptide and natural vitamin C.

As for the composition of natural vitamin C and a fish scale collagen peptide according to the present invention, the used fish scale collagen peptide is a bioactive polymeric substance obtained by enzymatic dehydration condensation from amino acid molecules according to a certain order, and it has a certain spatial structure that can enclose the molecules of natural vitamin C; and the molecules of the natural vitamin C are thus protected from being destroyed, such that the natural vitamin C is preserved, and the destruction of vitamin by ambient conditions, such as temperature, oxygen, illumination and the like, are reduced, thereby the contents of vitamin C in the end products are maintained at a relatively high level. Detections indicated that the loss rate of the natural vitamin C in the end product can be reduced to about 10%, which means that the loss of the natural vitamin C during the preparation process is greatly decreased. This has a great promoting effect on achieving the industrial production of the natural vitamin C.

As to the composition of the natural vitamin C and a fish scale collagen peptide according to the present invention, using both of the components together achieve a better synergistic effect. The antioxidant ability of the natural vitamin C can enhance and consolidate the anti-aging, cosmologic, and tendon and bone strengthening functions of the fish scale collagen peptide; and the fish scale collagae peptide can enhance blood vessel elasticity, which greatly helps natural vitamin C in preventing scorbutus and improving fragile capillary vessels by, and facilitates restoring the elasticity of the blood vessels and improving gingival bleeding by natural vitamin C. Moreover, the natural vitamin C has the effects of maintaining the elasticity of the skin as well as lightening spots, and the fish scale collagen peptide also has the effects of restoring elasticity and moisturizing, thus, the use of the both in combination with each other can on the one hand rapidly compensate for collagen losses in the body, and on the other hand, can keep the skin nourishing and radiant, so as to achieve the cosmologic and health caring effects from the inside out.

In addition, the vitamin C has the effects of strengthening cellular tissues and facilitating collagen synthesis. In the composition prepared in the present invention, the vitamin C and the fish scale collagen peptide exist in mixture with each other, thus, exogenous collagens can be supplemented and it is further beneficial to the generation of collagens in the human body itself, resulting in a duplicate health caring function.

DETAILED DESCRIPTION OF THE EMBODIMENTS

In the following, the technical solutions in the present invention are clearly and completely described in conjunction with examples of the present invention. Obviously, the described examples are merely partial examples of the present invention, rather than all the examples. Based on the examples in the present invention, all other examples that could be obtained by a person skilled in the art without inventive efforts fall within the scope of protection claimed in the present invention.

Example 1

A composition containing natural vitamin C and a fish scale collagen peptide comprises the following components by mass: 0.1 g of the natural vitamin C and 98 g of the fish scale collagen peptide.

A method of preparing the composition containing natural vitamin C and a fish scale collagen peptide comprises the following steps of:

(1) selecting high-quality fish scales from Hainan region as a raw material, and immersing the same in edible vinegar for softening under a negative pressure of 0.01 MPa for 30 min with a temperature being controlled at 70° C.;

(2) cleaning, drying and sterilizing the softened fish scales, and successively adding, based on the weight of fish scales, 5 times the weight of water and 1% of neutral protease for enzymatic hydrolysis, wherein during the enzymatic hydrolysis process, a temperature is controlled at 30° C., duration of the enzymatic hydrolysis is 2 hours, and a pressure is controlled at 0.01 MPa;

(3) adding activated carbon 1% of the weight of the fish scales, with a pressure being controlled at 0.01 MPa and a temperature being controlled at 20° C., for decoloration and deodorization for 30 min, and filtering out insoluble substances, to give an enzymatic-hydrolyzed fish scale collagen peptide solution;

(4) concentrating, at 60° C. under 0.01 MPa, the resultant fish scale collagen peptide solution to 30% of the volume thereof, and obtaining the fish scale collagen peptide by falling film evaporation and drying, with a temperature being set at 100° C.;

(5) weighing the natural vitamin C and the fish scale collagen peptide at a mass ratio respectively, and based on the total mass of the fish scale collagen peptide and the natural vitamin C, adding 5 times the weight of ultrapure water into the fish scale collagen peptide to prepare an aqueous solution, wherein during mixing process, a temperature is controlled at 30° C. and a pressure is controlled at 0.01 MPa;

(6) adding citric acid to adjust the pH value of the aqueous solution of the fish scale collagen peptide to 5, and adding a formula amount of the natural vitamin C to prepare a mixed solution of the natural vitamin C and the fish scale collagen peptide, wherein during the mixing process, a temperature is kept at 30° C. and a pressure is kept at 0.01 MPa;

(7) vacuum concentrating the mixed solution obtained in the step (6) under reduced pressure to give a concentrate of ¼ of the original volume, wherein during the concentration process, a temperature is controlled at 30° C. and a pressure is controlled at 0.01 MPa; and (8) spray drying the concentrate, obtained in the step (7), at 100° C. to give the composition of natural vitamin C and a fish scale collagen peptide; wherein the temperature of spray drying is controlled at 100° C.

Example 2

A composition containing natural vitamin C and a fish scale collagen peptide comprises the following components by mass: 2.5 g of the natural vitamin C and 99 g of the fish scale collagen peptide.

A method of preparing the composition containing natural vitamin C and a fish scale collagen peptide comprises the following steps of:

(1) selecting fish scales from Hainan region as a raw material, and immersing the same in edible vinegar for softening under a pressure of 0.09 MPa for 50 min, with a temperature being controlled at 90° C.;

(2) cleaning, drying and sterilizing the softened fish scales, and successively adding, based on the weight of fish scales, 20 times the weight of water and 4% of alkali protease for enzymatic hydrolysis, wherein during the enzymatic hydrolysis process, a temperature is controlled at 50° C., duration of the enzymatic hydrolysis is 6 hours, and a pressure is controlled at 0.09 MPa;

(3) adding activated carbon 4% of the weight of the fish scales, with a pressure being controlled at 0.09 MPa and a temperature being controlled at 30° C., for decoloration and deodorization for 40 min; and filtering out insoluble substances, to give an enzymatic-hydrolyzed fish scale collagen peptide solution;

(4) concentrating, at 70° C. under 0.09 MPa, the resultant fish scale collagen peptide solution to 50% of the volume thereof, and obtaining the fish scale collagen peptide by falling film evaporation and drying, with a temperature being set at 120° C.;

(5) weighing the natural vitamin C and the fish scale collagen peptide at a mass ratio respectively, and adding ultrapure water into the fish scale collagen peptide, wherein based on the total mass of the natural vitamin C and the fish scale collagen peptide, the mass of the ultrapure water is 6 times the total mass, and during mixing process, a temperature is controlled at 30° C. and a pressure is controlled at 0.05 MPa;

(6) adding malic acid to adjust the pH value to 6, and adding a formula amount of the natural vitamin C to prepare a mixed solution of the natural vitamin C and the fish scale collagen peptide, wherein during the mixing process, a temperature is controlled at 40° C. and a pressure is controlled at 0.05 MPa;

(7) concentrating the mixed solution, obtained in the step (6), to a concentrate of ⅓ of the original volume, wherein during the concentration process, a temperature is controlled at 40° C. and a pressure is controlled at 0.05 MPa; and (8) cold drying the concentrate obtained in the step (7), to give the composition of natural vitamin C and a fish scale collagen peptide, wherein during the cold drying process, a temperature is controlled at 40° C., and a pressure is controlled at 0.05 MPa.

Example 3

A composition containing natural vitamin C and a fish scale collagen peptide comprises the following components by mass: 5 g of the natural vitamin C and 99.9 g of the fish scale collagen peptide.

A method of preparing the composition containing natural vitamin C and a fish scale collagen peptide comprises the following steps of:

(1) selecting fish scales from Hainan region as raw material, and immersing the same in edible vinegar for softening at a pressure of 0.05 MPa for 40 min, with a temperature being controlled at 80° C.;

(2) cleaning, drying and sterilizing the softened fish scales, and successively adding, based on the weight of fish scales, 12 times the weight of water and 3% of alkali protease for enzymatic hydrolysis, wherein during the enzymatic hydrolysis process, a temperature is controlled at 40° C., duration of the enzymatic hydrolysis is 4 hours, and a pressure is controlled at 0.05 MPa;

(3) adding activated carbon 2% of the weight of the fish scales, with a pressure being controlled at 0.05 MPa and a temperature being controlled at 25° C., for decoloration and deodorization for 35 min; and filtering out insoluble substances, to give an enzymatic-hydrolyzed fish scale collagen peptide solution;

(4) concentrating, at 65° C. under a decreased pressure, the resultant fish scale collagen peptide solution to 40% of the volume thereof, and obtaining the fish scale collagen peptide by falling film evaporation and drying, with a temperature being set at 110° C.;

(5) weighing the natural vitamin C and the fish scale collagen peptide at a mass ratio respectively, and adding ultrapure water into the fish scale collagen peptide to form an aqueous solution, wherein based on the total mass of the natural vitamin C and the fish scale collagen peptide, the mass of the ultrapure water is 7 times the total mass, and during the mixing process, a temperature is controlled at 55° C., and a pressure is controlled at 0.09 MPa;

(6) adding citric acid to adjust the pH value to 7, and adding a formula amount of the natural vitamin C to prepare a mixed solution of the natural vitamin C and the fish scale collagen peptide, wherein during the mixing process, a temperature is controlled at 55° C. and a pressure is controlled at 0.09 MPa;

(7) concentrating the mixed solution, obtained in the step (6), to a concentrate of ½ of the original volume, wherein during the concentration process, a temperature is controlled at 55° C. and a pressure is at 0.09 MPa; and (8) freeze drying the concentrate obtained in the step (7), to give the composition of natural vitamin C and a fish scale collagen peptide, wherein during the drying process, a temperature is controlled at −20° C., and a pressure is controlled at 0.09 MPa.

Example 4

A composition containing natural vitamin C and a fish scale collagen peptide comprises the following components by mass: 0.1 g of the natural vitamin C and 99.9 g of the fish scale collagen peptide.

A method of preparing the composition containing natural vitamin C and a fish scale collagen peptide comprises the following steps of:

(1) selecting fish scales from Hainan region as a raw material, and immersing the same in edible vinegar for softening at a pressure of 0.01 MPa for 40 min, with a temperature being controlled at 80° C.;

(2) cleaning, drying and sterilizing the softened fish scales, and successively adding, based on the weight of fish scales, 12 times the weight of water and 1% of alkali protease for enzymatic hydrolysis, wherein during the enzymatic hydrolysis process, a temperature is controlled at 50° C., duration of the enzymatic hydrolysis is 4 hours, and a pressure is controlled at 0.05 MPa;

(3) adding activated carbon 2% of the weight of the fish scales, with a pressure being controlled at 0.05 MPa and a temperature being controlled at 20° C., for decoloration and deodorization for 35 min; and filtering out insoluble substances, to give an enzymatic-hydrolyzed fish scale collagen peptide solution;

(4) concentrating, at 60° C. under 0.09 MPa, the resultant fish scale collagen peptide solution to 50% of the volume thereof, and obtaining the fish scale collagen peptide by falling film evaporation and drying, with a temperature being set at 100° C.;

(5) weighing the natural vitamin C and the fish scale collagen peptide at a mass ratio respectively, and adding ultrapure water into the fish scale collagen peptide to form an aqueous solution; wherein based on the total mass of the natural vitamin C and the fish scale collagen peptide, the mass of the ultrapure water is 7 times the total mass; and during the mixing process, a temperature is controlled at 55° C. and a pressure is controlled at 0.07 MPa;

(6) adding malic acid to adjust the pH value to 7, and adding a formula amount of the natural vitamin C to prepare a mixed solution of the natural vitamin C and the fish scale collagen peptide, wherein during the mixing process, a temperature is controlled at 55° C. and a pressure is controlled at 0.01 MPa;

(7) concentrating the mixed solution, obtained in the step (6), to a concentrate of ½ of the original volume, wherein during the concentration process, a temperature is controlled at 55° C. and a pressure is at 0.01 MPa; and (8) freeze drying the concentrate obtained in the step (7), to give the composition of natural vitamin C and a fish scale collagen peptide, wherein during the drying process, a temperature is controlled at −10° C., and a pressure is controlled at 0.01 MPa.

Example 5

A composition containing natural vitamin C and a fish scale collagen peptide comprises the following components by mass: 2.6 g of the natural vitamin C and 99 g of the fish scale collagen peptide.

A method of preparing the composition containing natural vitamin C and a fish scale collagen peptide comprises the following steps of:

(1) selecting fish scales as a raw material, and immersing the same in edible vinegar for softening at a pressure of 0.05 MPa for 50 min, with the temperature being controlled at 70° C.;

(2) cleaning, drying and sterilizing the softened fish scales, and successively adding, based on the weight of fish scales, 5 times the weight of water and 3% of alkali protease for enzymatic hydrolysis, wherein during the enzymatic hydrolysis process, a temperature is controlled at 30° C., duration of the enzymatic hydrolysis is 2 hours, and a pressure is controlled at 0.01 MPa;

(3) adding activated carbon 2% of the weight of the fish scales, with a pressure being controlled at 0.09 MPa and a temperature being controlled at 25° C., for decoloration and deodorization for 40 min, and filtering out insoluble substances, to give an enzymatic-hydrolyzed fish scale collagen peptide solution;

(4) concentrating, at 70° C. under 0.01 MPa, the resultant fish scale collagen peptide solution to 30% of the volume thereof, and obtaining the fish scale collagen peptide by falling film evaporation and drying, with a temperature being set at 110° C.;

(5) weighing the natural vitamin C and the fish scale collagen peptide at a mass ratio respectively, and adding ultrapure water into the fish scale collagen peptide to form an aqueous solution, wherein based on the total mass of the natural vitamin C and the fish scale collagen peptide, the mass of the ultrapure water is 5 times the total mass, and during the mixing process, a temperature is controlled at 40° C., and a pressure is controlled at 0.05 MPa;

(6) adding citric acid to adjust the pH value to 5, and adding a formula amount of the natural vitamin C to prepare a mixed solution of the natural vitamin C and the fish scale collagen peptide, wherein during the mixing process, a temperature is controlled at 40° C. and a pressure is controlled at 0.05 MPa;

(7) concentrating the mixed solution obtained in the step (6) to a concentrate of ¼ of the original volume, wherein during the concentration process, a temperature is controlled at 30° C. and a pressure is at 0.05 MPa; and (8) cold drying the concentrate obtained in the step (7), to give a composition of natural vitamin C and a fish scale collagen peptide, wherein during the drying process, a temperature is controlled at 52° C., and a pressure is at 0.05 MPa.

Example 6

A composition containing natural vitamin C and a fish scale collagen peptide comprises the following components by mass: 5 g of the natural vitamin C and 99 g of the fish scale collagen peptide.

A method of preparing the composition containing natural vitamin C and a fish scale collagen peptide comprises the following steps of:

(1) selecting high-quality fish scales as a raw material, and immersing the same in edible vinegar for softening at a pressure of 0.09 MPa for 30 min, with a temperature being controlled at 90° C.;

(2) cleaning, drying and sterilizing the softened fish scales, and successively adding, based on the weight of fish scales, 20 times the weight of water and 4% of alkali protease for enzymatic hydrolysis, wherein during the enzymatic hydrolysis process, a temperature is controlled at 40° C., duration of the enzymatic hydrolysis is 6 hours, and a pressure is controlled at 0.09 MPa;

(3) adding activated carbon 1% of the weight of the fish scales, with a pressure being controlled at 0.01 MPa and a temperature being controlled at 30° C., for decoloration and deodorization for 30 min, and filtering out insoluble substances, to give an enzymatic-hydrolyzed fish scale collagen peptide solution;

(4) concentrating, at 65° C. under 0.05 MPa, the resultant fish scale collagen peptide solution to 40% of the volume thereof, and obtaining the fish scale collagen peptide by falling film evaporation and drying, with the temperature being set at 120° C.;

(5) weighing the natural vitamin C and the fish scale collagen peptide at a mass ratio respectively, and adding ultrapure water into the fish scale collagen peptide to form an aqueous solution, wherein based on the total mass of the natural vitamin C and the fish scale collagen peptide, the mass of the ultrapure water is 6 times the total mass, and during mixing process, a temperature is controlled at 30° C., and a pressure is controlled at 0.09 MPa;

(6) adding malic acid to adjust the pH value to 6, and adding a formula amount of the natural vitamin C to prepare a mixed solution of the natural vitamin C and the fish scale collagen peptide, wherein during the mixing process, a temperature is controlled at 40° C. and a pressure is controlled at 0.09 MPa;

(7) concentrating the mixed solution obtained in the step (6) to a concentrate of ⅓ of the original volume, wherein during the concentration process, a temperature is controlled at 30° C. and a pressure is at 0.09 MPa; and (8) spray drying the concentrate obtained in the step (7), to give the composition of natural vitamin C and a fish scale collagen peptide, wherein during the drying process, a temperature is controlled at 140° C.

In the above-mentioned examples, the natural vitamin C used is extracted from Acerola cherry.

Determination of Vitamin C Content in the Composition Containing Natural Vitamin C and a Fish Scale Collagen Peptide According to the Present Invention As to experimental groups thereof, compositions were prepared according to the following solutions respectively:

Solution 1: preparation was performed according to the formula and production process of Example 1;

Solution 2: preparation was performed according to the formula and production process of Example 2;

Solution 3: preparation was performed according to the formula and production process of Example 3;

Solution 4: preparation was performed according to the formula and production process of Example 4;

Solution 5: preparation was performed according to the formula and production process of Example 5; and Solution 6: preparation was performed according to the formula and production process of Example 6.

As to control groups thereof, only natural vitamin C used in the above-mentioned examples was added, with the mass thereof equal to the total mass of the natural vitamin C and the fish scale collagen peptide in the above-mentioned experimental groups respectively, and treatment was performed according to the solution of the corresponding experimental group. With reference to the detection method for detecting the content of vitamin C in vitamin C tablets in *Pharmacopoeia of the People's Republic of China* (2010), the contents of vitamin C in the end products obtained in the control groups and in the experimental groups were determined respectively, and the loss rates of vitamin C in the end products obtained from different preparation methods were calculated. The results thereof are shown in Table 1.

TABLE 1

Comparison of vitamin C loss rates of different preparation methods

| Solution No. | | Concentration of vitamin C inputted in the production (g/100 g) | Concentration of vitamin C in the end product (g/100 g) | Loss rate of vitamin C (%) |
|---|---|---|---|---|
| 1 | Experimental group | 0.102 | 0.092 | 9.804 |
|   | Control group | 100 | 15.67 | 84.33 |
| 2 | Experimental group | 2.463 | 2.197 | 10.8 |
|   | Control group | 100 | 17.86 | 82.14 |
| 3 | Experimental group | 4.766 | 4.532 | 4.91 |
|   | Control group | 100 | 19.25 | 80.75 |
| 4 | Experimental group | 0.1 | 0.089 | 11 |
|   | Control group | 100 | 15.73 | 84.27 |
| 5 | Experimental group | 2.584 | 2.347 | 9.189 |
|   | Control group | 100 | 14.19 | 85.81 |
| 6 | Experimental group | 4.808 | 4.372 | 9.062 |
|   | Control group | 100 | 18.61 | 81.39 |

Vitamin C, particularly natural vitamin C, is exceedingly unstable in nature, and would be easily oxidized and decomposed under conditions including heating, illumination, contact with oxygen and so forth, resulting in loss of the functions. Studies showed that natural vitamin C contained in vegetables and fruits can be damaged when being heated to 60-80° C. This property of the nature vitamin C severely limits the applications of natural vitamin C in the fields of medical treatment, health care and research. It can be seen from Table 1 that after end products were prepared, the loss rates of vitamin C in the control groups, in which the vitamin C was merely added, were all greater than 70%. However, in the case of utilizing the preparation methods for preparing a composition from natural vitamin C and a fish scale collagen peptide provided in the 6 examples of the present invention, the loss rates of vitamin C in the end products were about 10%, which indicates a significant reduction in the loss rates of vitamin C, compared with the control groups without the addition of fish scale collagen peptide. It showed that the preparation methods provided in the present invention can efficiently protect vitamin C from being destroyed with no requirement of adding any further additives during the preparation process. The concentrations of vitamin C in the end products were maintained at a relatively high level, which has a great promoting effect on achieving the plant-scale industrial production of natural vitamin C.

Comparison of Therapeutic Effects of the Compositions Containing Natural Vitamin C and a Fish Scale Collagen Peptide According to the Present Invention (I) Exploration of the Therapeutic Effects of the Compositions According to the Present Invention and that of Respective Administration of the Natural Vitamin C and the Fish Scale Collagen Peptide 132 patients were selected at random, wherein each patient respectively showed, to different degrees, symptoms such as anorexia, dull complexion, xeroderma, anetodermia, arthralgia, easy fatigability, debilitation, dizziness, and hypertension and so on, and had immune hypofunction, which resulted in a far higher morbidity of various infectious diseases than the average level of respective same age group. The patients were divided into 12 groups at random, each with 11 persons. 6 groups thereof served as experimental groups, and were respectively administrated the compositions of natural vitamin C and a fish scale collagen peptide prepared through the methods according to the present invention, while the other 6 groups served as control groups and were respectively administrated fish scale collagen peptide powders and the natural vitamin C, the dosages of which were respectively equivalent to the those of the corresponding example. After a three-month treatment, the therapeutic effects thereof were observed. And the therapeutic effects thereof were summarized in accordance with the following evaluation criteria. The therapeutic effects thereof are recorded in Table 2.

Cured: the symptoms disappeared and did not recur after drug withdrawal;

Effective: the symptoms were improved significantly, and partial symptoms recurred after drug withdrawal; and Ineffective: the symptoms were not improved.

TABLE 2

Exploration (I) of the therapeutic effects of the compositions according to the present invention

| No. | Treatment method | Total number/ person | Cured/ person | Effective/ person | Ineffective/ person | Total effective rate/% |
|---|---|---|---|---|---|---|
| Example 1 | Experimental group | 11 | 3 | 6 | 2 | 81.82 |
|  | Control group | 11 | 2 | 6 | 3 | 72.73 |
| Example 2 | Experimental group | 11 | 4 | 5 | 2 | 81.82 |
|  | Control group | 11 | 5 | 5 | 1 | 90.91 |
| Example 3 | Experimental group | 11 | 3 | 7 | 1 | 90.91 |
|  | Control group | 11 | 3 | 6 | 2 | 81.82 |
| Example 4 | Experimental group | 11 | 6 | 5 | 0 | 100 |
|  | Control group | 11 | 5 | 3 | 3 | 72.73 |
| Example 5 | Experimental group | 11 | 5 | 4 | 2 | 81.82 |
|  | Control group | 11 | 4 | 5 | 2 | 81.82 |
| Example 6 | Experimental group | 11 | 4 | 6 | 1 | 90.91 |
|  | Control group | 11 | 3 | 6 | 2 | 81.82 |

It can be seen from Table 2 that the total effective rates for the administration of the compositions of natural vitamin C and a fish scale collagen peptide according to the present invention were greater than 80%, wherein in Examples 3, 4 and 6, total effective rates thereof were significantly higher than those of the control groups. Furthermore, in Examples of the present invention, the composition is prepared from the natural vitamin C and the fish scale collagen peptide, thus on the one hand, the proportion can be adjusted according to the administration requirements of patients, and the two medicaments can be administrated at one time, making administration convenient; on the other hand, the preparation of the composition from the natural vitamin C and the fish scale collagen peptide can protect the natural vitamin C from being destroyed during the preparation process, which maintains the activity of the natural vitamin C to the greatest degree. Using the preparation method according to the present invention, the loss rate of the natural vitamin C during the preparation process was reduced to about 10% without adding further additives, and through administration to patients, the effective rate thereof was significantly higher than the effect of separate administration of the fish scale collagen peptide powders and the natural vitamin C.

(II) Comparison of the Therapeutic Effects of the Compositions Obtained in the Present Invention and that of Conventional Treatment 70 patients were selected at random, wherein each patient respectively showed, to different degrees, symptoms such as anorexia, dull complexion, xeroderma, anetodermia, arthralgia, easy fatigability, debilitation, dizziness, and hypertension and so on, and had immune hypofunction, which resulted in a far higher morbidity of various infectious diseases than the average level of respective same age group. The patients were divided into 7 groups at random, each with 10 persons, wherein 6 groups served as experimental groups and were respectively administrated the compositions of natural vitamin C and a fish scale collagen peptide obtained from the 6 examples in the present invention, while the 7th group was given a conventional treatment. After three months, the rehabilitation conditions of the patients were recorded. And the results thereof were recorded in Table 3. The evaluation on the therapeutic effects was made with reference to the following criteria:

Cured: the symptoms disappeared and did not recur after drug withdrawal;

Effective: the symptoms were improved significantly, and partial symptoms recurred after drug withdrawal; and Ineffective: the symptoms were not improved.

TABLE 3

Explorations (II) of the therapeutic effects of the compositions according to the present invention

| No. | Total number/ person | Cured/ person | Effective/ person | Ineffective/ person | Total effective rate/% |
|---|---|---|---|---|---|
| Example 1 | 10 | 2 | 5 | 3 | 70 |
| Example 2 | 10 | 4 | 4 | 2 | 80 |
| Example 3 | 10 | 3 | 5 | 2 | 80 |
| Example 4 | 10 | 1 | 6 | 3 | 70 |
| Example 5 | 10 | 2 | 6 | 2 | 80 |
| Example 6 | 10 | 5 | 4 | 1 | 90 |
| Control group | 10 | 3 | 4 | 3 | 70 |

It can be seen from Table 2 that the total effective rates of the compositions of natural vitamin C and a fish scale collagen peptide according to the present invention were greater than 70%, which was significantly higher than that of the control group. It showed that the composition according to the present invention had a therapeutic effect on the above-mentioned symptoms. Moreover, as to the composition according to the present invention, the vitamin C and the fish scale collagen peptide thereof are both derived from natural plants or animals, and no further additive is added during the preparation process, which means it contains no chemical agents, has no side effects, would do no damage to the body, and thus can be used as health caring product for a long time, and has good health caring function.

In the comparison process of the two groups of experiments above, it was also found that the composition according to the present invention had a particularly significant therapeutic effect on backache or joint pain. In Exploration (I), 47 patients among the patients participating in the experiments had the symptom of backache or joint pain, and after a three-month treatment, 46 patients showed a significant relief or complete disappearance of the symptom, and only one patient had no improvement in the symptom, and the total effective rate reached 97.87%; and in Exploration (II), 29 patients in the experimental groups had the symptom of backache or joint pain, and after treatment, 27 patients showed a significant relief or complete disappearance of the symptom, and the total effective rate thereof reached 93.10%. Moreover, middle-aged and elderly patients having the above-mentioned symptoms in the experimental groups showed a significant relief or complete disappearance of the symptom of backache or joint pain after treatment, and the therapeutic effect is exceedingly significant.

The above-mentioned description is merely preferred examples of the present invention, and does not intend to limit the present invention; and any modifications, equivalent substitutions and improvements made within the spirit and principle of the present invention shall all fall within the scope of protection of the present invention.

The invention claimed is:

1. A method of preparing the composition of natural vitamin C and a fish scale collagen peptide comprising following steps: (1) adding ultrapure water into a formula amount of the fish scale collagen peptide to prepare an aqueous solution; (2) adding a pH regulator into the aqueous solution of the fish scale collagen peptide to adjust a pH value to 5-7; and adding, under a negative pressure condition, a formula amount of the natural vitamin C to prepare a mixed solution of the natural vitamin C and the fish scale collagen peptide; (3) concentrating the mixed solution, obtained in the step (2), under a negative pressure to give a concentrate of ¼-½ of an original volume; and (4) cold drying, freeze drying or spray drying the concentrate under a negative pressure condition, to give the composition of natural vitamin C and the fish scale collagen peptide.

2. The method of preparing the composition of natural vitamin C and a fish scale collagen peptide according to claim 1, wherein in the step (1), mass of the ultrapure water is 5-7 times the total mass of the natural vitamin C and the fish scale collagen peptide.

3. The method of preparing the composition of natural vitamin C and a fish scale collagen peptide according to claim 1, wherein the pH regulator used in the step (2) for regulating a pH value is citric acid or malic acid.

4. The method of preparing the composition of natural vitamin C and a fish scale collagen peptide according to claim 1, wherein in the step (2) and the step (3), temperatures are controlled at 30-55° C. during processes of mixing and concentration.

5. The method of preparing the composition of natural vitamin C and a fish scale collagen peptide according to claim 1, wherein in the step (4), a temperature for spray drying is between 100 and 140° C.; a temperature during the process of cold drying is controlled at 40-52° C.; and a temperature during the process of freeze drying is controlled at −20 to −10° C.

6. The method of preparing the composition of natural vitamin C and a fish scale collagen peptide according to claim 1, wherein a range for the negative pressures (P) in the steps (2), (3) and (4) is: $0.01\ \text{MPa} \leq P < 0.1\ \text{MPa}$.

7. The method of preparing the composition of natural vitamin C and a fish scale collagen peptide according to claim 1, wherein the natural vitamin C is extracted from Acerola cherry.

8. The method of preparing the composition of natural vitamin C and a fish scale collagen peptide according to claim 1, wherein a method of preparing the fish scale collagen peptide comprises following steps of: a. selecting fish scales as a raw material, and immersing the same in edible vinegar for softening under a negative pressure; b. cleaning, drying and sterilizing the softened fish scales, and adding water and an enzyme successively for enzymatic hydrolysis, wherein pressure is controlled as being negative, during a process of the enzymatic hydrolysis; c. adding activated carbon for decoloration and deodorization under a negative pressure, and filtering out insoluble substances, to give an enzymatic-hydrolyzed fish scale collagen peptide solution; and d. concentrating, under a negative pressure, the fish scale collagen peptide solution to 30-50% of the volume thereof, and obtaining the fish scale collagen peptide by falling film evaporation and drying.

9. The method of preparing the composition of natural vitamin C and a fish scale collagen peptide according to claim 8, wherein a range for the negative pressures (P) in the steps a, b, c and d is: $0.01\ \text{MPa} \leq P < 0.1\ \text{MPa}$.

10. The method of preparing the composition of natural vitamin C and a fish scale collagen peptide according to claim 8, wherein in the step a, temperature of softening is 70-90° C., and duration of softening is 30-50 min.

11. The method of preparing the composition of natural vitamin C and a fish scale collagen peptide according to claim 8, wherein in the step b, a weight of water added is 5-20 times that of the fish scales, a weight of the enzyme added is 1%-4% of that of the fish scales, and the enzymatic hydrolysis is performed at a temperature controlled at 30-50° C., for 2-6 h.

12. The method of preparing the composition of natural vitamin C and a fish scale collagen peptide according to claim 8, wherein the enzyme is selected from the group consisting of neutral proteases and alkali proteases.

13. The method of preparing the composition of natural vitamin C and a fish scale collagen peptide according to claim 8, wherein in the step c, a proportion of the added activated carbon to a weight of the fish scales is 1%-4%, and the decoloration and deodorization are performed at a temperature controlled at 20-30° C., for 30-40 min.

14. The method of preparing the composition of natural vitamin C and a fish scale collagen peptide according to claim 8, wherein, in the step d, a temperature is controlled at 60-70° C. during a process of the concentrating, and a temperature is controlled at 100-140° C. during a process of the drying.

15. The method of preparing the composition of natural vitamin C and a fish scale collagen peptide according to claim 2, wherein a range for the negative pressures (P) in the steps (2), (3) and (4) is: $0.01\ \text{MPa} \leq P < 0.1\ \text{MPa}$.

16. The method of preparing the composition of natural vitamin C and a fish scale collagen peptide according to claim 3, wherein a range for the negative pressures (P) in the steps (2), (3) and (4) is: $0.01\ \text{MPa} \leq P < 0.1\ \text{MPa}$.

* * * * *